US00PP18197P2

(12) United States Plant Patent
van Buren

(10) Patent No.: US PP18,197 P2
(45) Date of Patent: Nov. 13, 2007

(54) ***HYDRANGEA* PLANT NAMED 'RED SENSATION'**

(50) Latin Name: *Hydrangea macrophylla*
Varietal Denomination: Red Sensation

(75) Inventor: Gert van Buren, Hillegom (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/454,066

(22) Filed: Jun. 15, 2006

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent Bell
(74) *Attorney, Agent, or Firm*—C. A. Whealy

(57) ABSTRACT

A new and distinct cultivar of *Hydrangea* plant named 'Red Sensation', characterized by its upright and mounded plant habit; strong roots and stems; flowering during first year of production; and large inflorescences with light red purple-colored flowers.

1 Drawing Sheet

Botanical designation: *Hydrangea macrophylla.*
Cultivar denomination: 'Red Sensation'.

BACKGROUND OF THE INVENTION

The present invention relates to a new and distinct cultivar of *Hydrangea,* botanically known as *Hydrangea macrophylla* and hereinafter referred to by the name 'Red Sensation'.

The new *Hydrangea* is a naturally-occurring branch mutation of the *Hydrangea macrophylla* cultivar Early Sensation, not patented. The new *Hydrangea* was discovered and selected by the Inventor in a controlled environment in Hillegom, The Netherlands in 2001.

Asexual reproduction of the new *Hydrangea* by vegetative cuttings in a controlled environment in Hillegom, The Netherlands since 2001, has shown that the unique features of this new *Hydrangea* are stable and reproduced true to type in successive generations.

SUMMARY OF THE INVENTION

The cultivar Red Sensation has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Red Sensation'. These characteristics in combination distinguish 'Red Sensation' as a new and distinct cultivar of *Hydrangea:*

1. Upright and mounded plant habit.
2. Strong roots and stems.
3. Flowers first year of production.
4. Large inflorescences with light red purple-colored flowers.

Plants of the new *Hydrangea* differ from plants of the parent, the cultivar Early Sensation, primarily in flower color as plants of the cultivar Early Sensation have pink-colored flowers.

Plants of the new *Hydrangea* can be compared to plants of the cultivar First Red, disclosed in U.S. Plant patent application Ser. No. 11/509,516. Plants of the new *Hydrangea* differ from plants of the cultivar First Red primarily in flower color as plants of the cultivar First Red have darker red purple-colored flowers.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new *Hydrangea.* The photograph comprises a side perspective view of a typical plant of 'Red Sensation' grown in a container.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and in the following description were grown in Hillegom, The Netherlands, in 5-liter containers in an outdoor nursery and under conditions which closely approximate commercial production conditions. During the production of the plants, day temperatures ranged from 10° C. to 30° C. and night temperatures ranged from 10° C. to 18° C. Plants of the new *Hydrangea* were about two years old when the photographs and description were taken during the early fall.

Botanical description: *Hydrangea macrophylla* cultivar 'Red Sensation'.

Parentage: Naturally-occurring branch mutation of the *Hydrangea macrophylla* cultivar Early Sensation, not patented.

Propagation:

*Type cutting.*—By vegetative cuttings.

*Time to initiate roots.*—About three weeks at temperatures of 14° C.

*Root description.*—Fine, fibrous, strong; white in color.

*Rooting habit.*—Freely branching.

Plant description:

*Form/growth habit.*—Upright and mounded plant habit; inverted triangle. Strong lateral branches; moderately vigorous growth habit.

*Plant height.*—About 30 cm.

*Plant diameter or area of spread.*—About 45 cm.

*Branching habit.*—When pinched, freely branching with about ten lateral branches per plant.

*Lateral branches.*—Length: About 19.5 cm. Diameter: About 5 mm. Internode length: About 4.9 cm. Texture: Smooth, glabrous. Strength: Strong. Color: 144A.

Foliage description:

*Arrangement.*—Opposite, simple.

*Length.*—About 8 cm.

*Width.*—About 5.8 cm.

*Shape.*—Broadly oval to broadly elliptic to oblong.

*Apex.*—Apiculate.

*Base.*—Acuminate.

*Margin.*—Serrate.

*Texture, upper and lower surfaces.*—Rugose; glabrous.

*Venation pattern.*—Pinnate.

*Color.*—Developing foliage, upper surface: 141A. Developing foliage, lower surface: 143A. Fully expanded foliage, upper surface: 137B; venation, 144C. Fully expanded foliage, lower surface: 138A to 138B; venation, 145C.

*Petiole.*—Length: About 1.4 cm. Diameter: About 3 mm. Texture, upper and lower surfaces: Smooth, glabrous. Color, upper and lower surfaces: 145A.

Flower description:

*Flower type and habit.*—Single flat flowers arranged on terminal panicles; panicles large and globular. Flowers face upright to outward. Flowers persistent. Flowers not fragrant.

*Natural flowering season.*—Continuous flowering from early June to September in Northern Europe. Plants flower during the first year of production.

*Flower longevity.*—Flowers last about three weeks on the plant.

*Quantity of flowers.*—Freely flowering; about 30 fertile flowers and about 105 sterile flowers per panicle.

*Panicle height.*—About 11.7 cm.

*Panicle diameter.*—About 16.3 cm.

*Flower diameter, fertile flowers.*—About 6 mm.

*Flower diameter, sterile flowers.*—About 4.5 cm.

*Flower depth (height), fertile flowers.*—About 5 mm.

*Flower depth (height), sterile flowers.*—About 9 mm.

*Flower buds, fertile and sterile flowers.*—Length: About 4 mm. Diameter: About 4 mm. Shape: Globular. Color: 65B; towards the base, 65D.

*Petals, fertile flowers only.*—Arrangement: Four in a single whorl. Length: About 4 mm. Width: About 2.5 mm. Shape: Ovate. Apex: Acute. Base: Attenuate. Margin: Entire. Texture, upper and lower surfaces: Smooth, glabrous. Color: When opening and fully opened, upper surface: 64C; towards the base, 65D. When opening and fully opened, lower surface: 65A; towards the base, 65D.

*Sepals, fertile flowers.*—Quantity per flower: Four in a single whorl; fused at base. Length: About 4 mm. Width: About 1.5 mm. Shape: Deltoid. Apex: Acute. Margin: Entire. Texture, upper and lower surfaces: Smooth, glabrous. Color: When opening and fully opened, upper surface: 144B; towards the apex, 146B. When opening and fully opened, lower surface: 144B; towards the apex, tinged with 65A to 65B.

*Sepals, sterile flowers.*—Quantity per flower: Four or five in a single whorl. Length: About 2.2 cm. Width: About 2.4 cm. Shape: Deltoid. Apex: Rounded to broadly acute. Base: Cuneate. Margin: Entire. Texture, upper and lower surfaces: Smooth, glabrous. Color: When opening and fully opened, upper surface: 64D. When opening and fully opened, lower surface: 63C.

*Pedicels, fertile and sterile flowers.*—Angle: About 25° from vertical. Strength: Strong. Length: About 2.2 cm. Diameter: About 1.5 mm. Color: 75D.

*Reproductive organs, fertile flowers only.*—Stamens: Quantity per flower: About eight. Filament length: About 2 mm. Filament color: N158D. Anther shape: Reniform. Anther length: About 1.5 mm. Anther color: 157C. Pollen amount: Scarce. Pollen color: N158D. Pistils: Pistil quantity per flower: About three. Pistil length: About 1.5 mm. Stigma shape: Lobed. Stigma color: 157D. Style length: About 0.5 mm. Style color: 157D. Ovary color: 154C to 154D.

*Seed/fruit.*—Seed and fruit development has not been observed.

Disease/pest resistance: Under commercial production conditions, plants of the new *Hydrangea* have not been observed to be resistant to pathogens or pests common to *Hydrangea*.

Temperature tolerance: Plants of the new *Hydrangea* have been shown to be tolerant to temperatures ranging from about 0° C. to about 35° C.

It is claimed:

1. A new and distinct *Hydrangea* plant named 'Red Sensation' as illustrated and described.

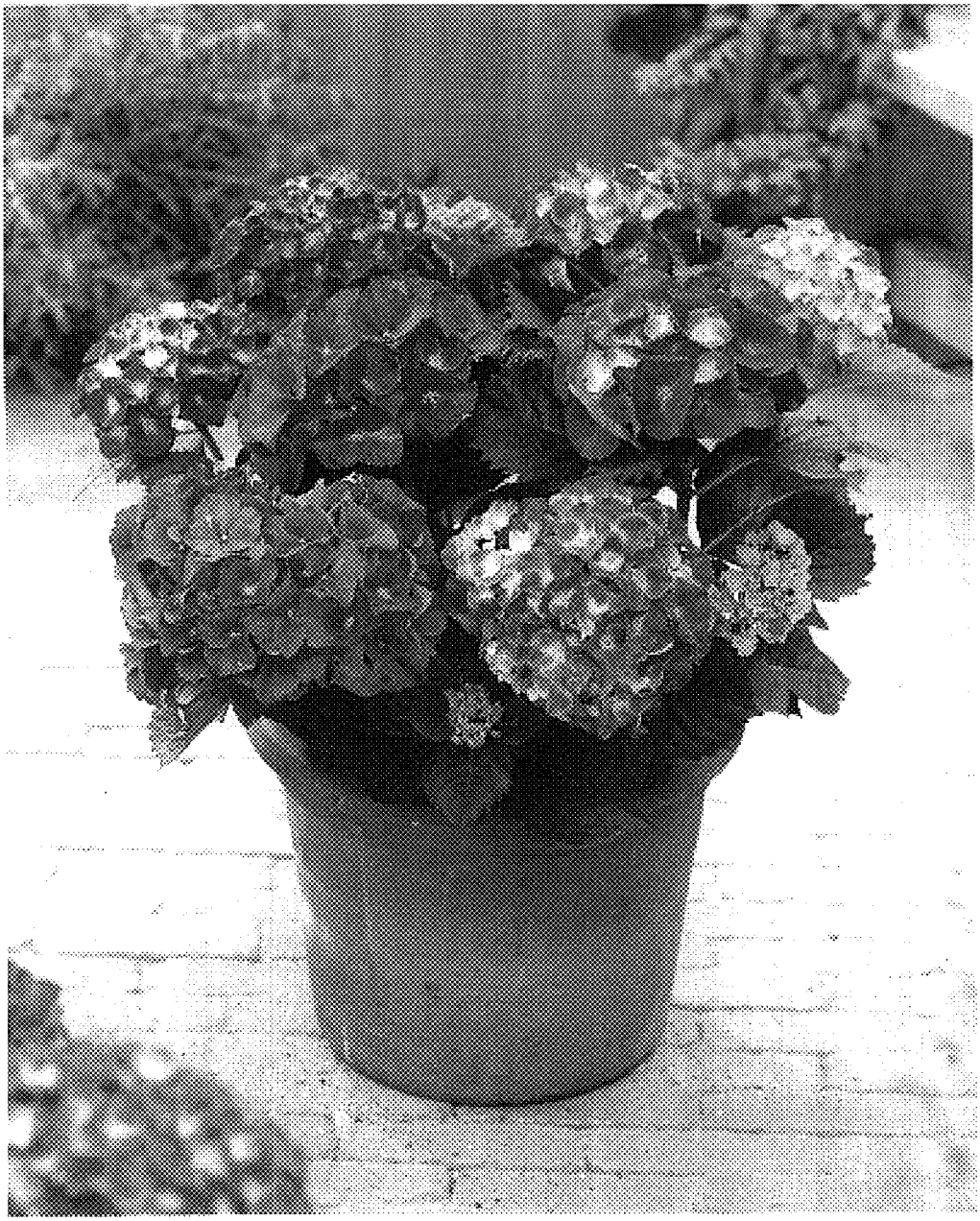

* * * * *